US009575069B2

(12) United States Patent
Menchen et al.

(10) Patent No.: US 9,575,069 B2
(45) Date of Patent: Feb. 21, 2017

(54) USE OF ANTIBODY-SURROGATE ANTIGEN SYSTEMS FOR DETECTION OF ANALYTES

(71) Applicant: APPLIED BIOSYSTEMS, LLC, Carlsbad, CA (US)

(72) Inventors: Steven Menchen, Fremont, CA (US); Joe Y. Lam, Castro Valley, CA (US); Zhaochun Ma, Sunnyvale, CA (US); Khairuzzaman Bashar Mullah, Union City, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

(21) Appl. No.: 14/074,931

(22) Filed: Nov. 8, 2013

(65) Prior Publication Data

US 2015/0198605 A1 Jul. 16, 2015

Related U.S. Application Data

(63) Continuation of application No. 12/705,746, filed on Feb. 15, 2010, now abandoned, which is a continuation of application No. 12/511,948, filed on Jul. 29, 2009, now abandoned, which is a continuation of application No. 11/375,825, filed on Mar. 15, 2006, now abandoned.

(60) Provisional application No. 60/662,412, filed on Mar. 15, 2005.

(51) Int. Cl.
G01N 33/58 (2006.01)
C07D 311/88 (2006.01)
G01N 33/532 (2006.01)

(52) U.S. Cl.
CPC ........... G01N 33/582 (2013.01); C07D 311/88 (2013.01); G01N 33/532 (2013.01); G01N 33/58 (2013.01)

(58) Field of Classification Search
CPC .................................................. G01N 35/582
USPC ............................................................ 435/4
See application file for complete search history.

(56) References Cited

U.S. PATENT DOCUMENTS

| | | |
|---|---|---|
| 4,434,236 A | 2/1984 | Freytag |
| 4,439,356 A | 3/1984 | Khanna et al. |
| 4,481,136 A | 11/1984 | Khanna et al. |
| 4,486,530 A | 12/1984 | David et al. |
| 4,933,471 A | 6/1990 | Lee |
| 5,002,582 A | 3/1991 | Guire et al. |
| 5,066,580 A | 11/1991 | Lee |
| 5,188,934 A | 2/1993 | Menchen et al. |
| 5,227,487 A | 7/1993 | Haugland et al. |
| 5,229,302 A | 7/1993 | Miyazaki et al. |
| 5,231,191 A | 7/1993 | Woo et al. |
| 5,314,817 A | 5/1994 | Schultz et al. |
| 5,366,860 A | 11/1994 | Bergot et al. |
| 5,391,171 A | 2/1995 | Schmieding |
| 5,391,711 A | 2/1995 | Funakoshi et al. |
| 5,436,134 A | 7/1995 | Haugland et al. |
| 5,493,012 A | 2/1996 | Rokita et al. |
| 5,562,100 A | 10/1996 | Kittrell et al. |
| 5,654,442 A | 8/1997 | Menchen et al. |
| 5,713,364 A | 2/1998 | DeBaryshe et al. |
| 5,721,099 A | 2/1998 | Still et al. |
| 5,750,409 A | 5/1998 | Herrmann et al. |
| 5,800,996 A | 9/1998 | Lee et al. |
| 5,840,999 A | 11/1998 | Benson et al. |
| 5,847,162 A | 12/1998 | Lee et al. |
| 5,863,727 A | 1/1999 | Lee et al. |
| 5,863,753 A | 1/1999 | Haugland et al. |
| 5,936,087 A | 8/1999 | Benson et al. |
| 5,945,526 A | 8/1999 | Lee et al. |
| 5,986,076 A | 11/1999 | Rothschild et al. |
| 6,005,113 A | 12/1999 | Wu et al. |
| 6,008,379 A | 12/1999 | Benson et al. |
| 6,017,712 A | 1/2000 | Lee et al. |
| 6,020,209 A | 2/2000 | Narang |
| 6,025,505 A | 2/2000 | Lee et al. |
| 6,051,719 A | 4/2000 | Benson et al. |
| 6,080,852 A | 6/2000 | Lee et al. |
| 6,080,868 A | 6/2000 | Lee et al. |
| 6,111,116 A | 8/2000 | Benson et al. |
| 6,232,075 B1 | 5/2001 | Williams |
| 6,248,884 B1 | 6/2001 | Lam et al. |
| 6,319,674 B1 | 11/2001 | Fulcrand et al. |
| 6,399,392 B1 | 6/2002 | Haugland et al. |
| 6,646,118 B2 | 11/2003 | Kwiatkowski et al. |
| 6,692,911 B2 | 2/2004 | Pack et al. |
| 6,770,439 B2 | 8/2004 | Singh et al. |
| 6,835,393 B2 | 12/2004 | Hoffman et al. |
| 6,969,769 B2 | 11/2005 | Worley et al. |
| 7,332,613 B2 | 2/2008 | Gygi et al. |
| 7,846,436 B2 | 12/2010 | Srivastava et al. |
| 2002/0177698 A1 | 11/2002 | Kwiatkowski et al. |

(Continued)

FOREIGN PATENT DOCUMENTS

| | | |
|---|---|---|
| EP | 050684 | 5/1982 |
| EP | 0313666 | 5/1989 |

(Continued)

OTHER PUBLICATIONS

Borresen, H. et al., "The Fluorescence of Guanine and Guanosine", Effects of Temperature and Viscosity on Fluorescence Polarization and Quenching, Acta Chemica Scandinavica, vol. 21, 1967, pp. 920-936.
Cotten, Matthew et al., "Receptor-Mediated Transport of DNA into Eukaryotic Cells", Methods Enzym, v. 217, 618-644, 1993, 618-644.
Daniels, M. et al., "Fluorescence of the Purine and Pyrimidine Bases of the Nucleic Acids in Neutral Aqueous Solution at 300 K", Science, New Series, vol. 171, No. 3972, 1971, pp. 675-677.
Edwards, et al., "Liposomes in analyses", Talanta,Elsevier, Amsterdam, NL, vol. 68, No. 5, http://dx.doi.org/10.1016/j.talanta.2005.08.044, Feb. 28, 2006, pp. 1421-1431.
Greene, T. W. , "Protective Groups in Organic Synthesis", John Wiley & Sons, 2nd Ed., 1991.

(Continued)

Primary Examiner — David Lukton

(57) ABSTRACT

Compositions, methods and kits for labeling proteins and uses in reporter systems for detecting, quantifying and/or characterizing analytes.

27 Claims, 3 Drawing Sheets

(56) References Cited

U.S. PATENT DOCUMENTS

Figures 1A, 1B, 1C, 1D, 1E:
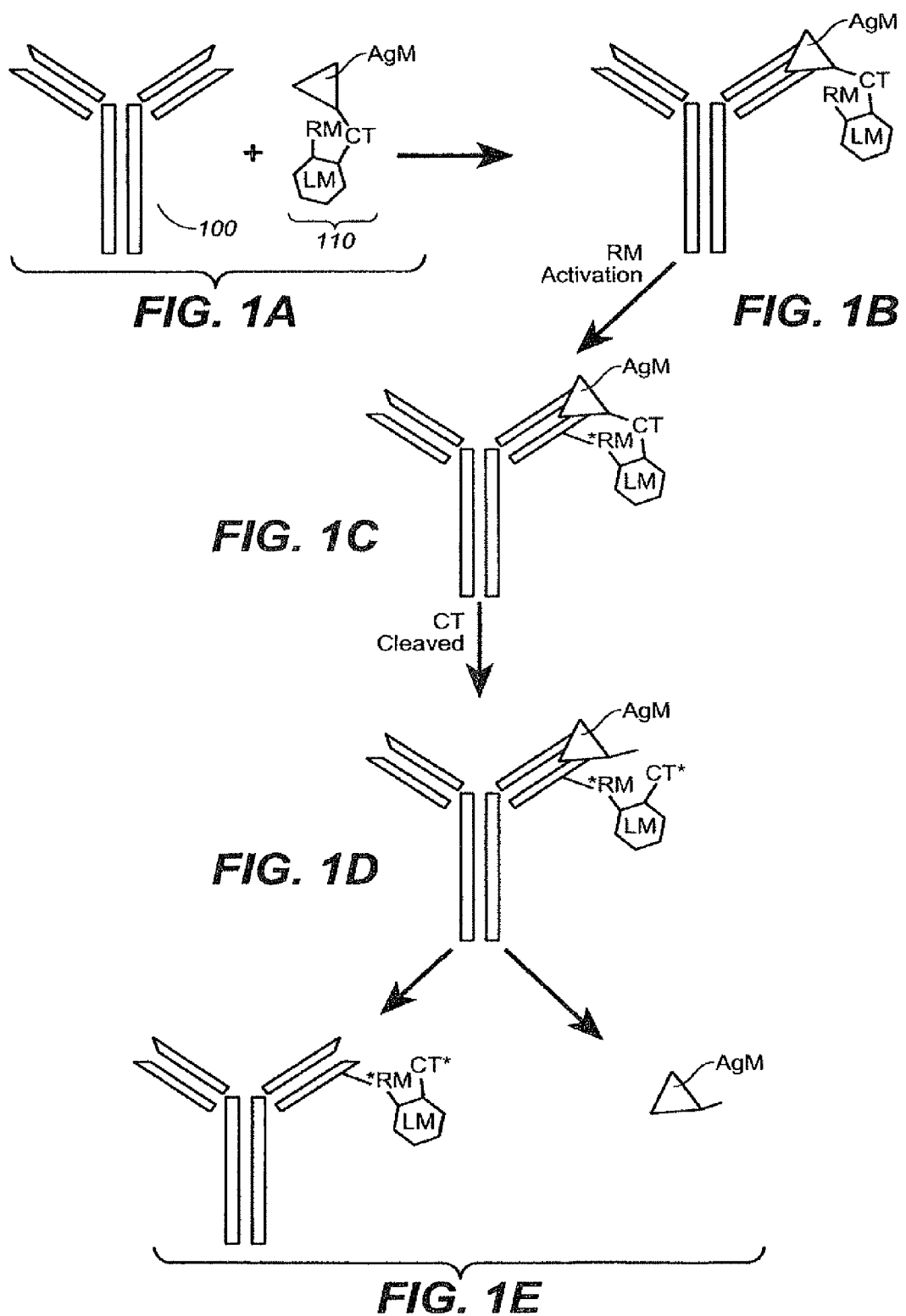

| | | | |
|---|---|---|---|
| 2004/0166529 A1 | 8/2004 | Singh et al. |
| 2004/0259164 A1 | 12/2004 | Gygi et al. |
| 2008/0081902 A1 | 4/2008 | Fang |
| 2010/0267938 A1 | 10/2010 | Menchen et al. |

FOREIGN PATENT DOCUMENTS

| | | |
|---|---|---|
| WO | WO-96/04405 | 2/1996 |
| WO | WO-97/36960 | 10/1997 |
| WO | WO-99/16832 | 4/1999 |
| WO | WO-99/27020 | 6/1999 |
| WO | WO-02/057739 | 7/2002 |
| WO | WO-03/035229 | 5/2003 |
| WO | WO-2004/051270 | 6/2004 |

OTHER PUBLICATIONS

Lee, et al., "DNA sequencing with dye-labeled terminators and T7 DNA polymerase: effect of C48 dyes and dNTPs on incorporation od dye-terminators and probability analysis of termination fragments,", *Nucleic Acids Research*, vol. 20, No. 10, 1992, 2471-2483.

Lee, L G. et al., "New energy transfer dyes for DNA sequencing", *Nucleic Acids Research*, vol. 25, No. 14, Jul. 1997, 2816-2822.

Mattson, G. et al., "A practical approach to crosslinking", *Mol Biol Reports*, vol. 17(3), Apr. 1993, 167-183.

Nakamura, N. et al., "Immunoassay Method for the Determination of Immunoglobulin G Using Bacterial Magnetic Particles", *Analytical Chemistry, American Chemical Society*. Columbus,US, vol. 63, No. 3, Feb. 1, 1991, pages 268-272.

PCT/US2006/009520, , "International Preliminary Report on Patentability", Sep. 18, 2007, 17 pgs.

PCT/US2006/009520, , "International Search Report", Nov. 20, 2006, 9 pgs.

PCT/US2006/009520, , "Written Opinion", Nov. 20, 2006, 16 pgs.

Rosenblum, B B. et al., "New dye-labeled terminators for improved DNA sequencing patterns", *Nucleic Acids Research*, vol. 25, No. 22, Nov. 1997, 4500-4504.

Sauer, M. et al., "New Fluorescent Dyes in the Red region for Biodiagnostics", *Journal of Fluorescence*, vol. 5(3), 1995, pp. 247-261.

Ullman, E. F. et al., "Fluorescent excitation transfer immunoassay. A general method for determination of antigens", *Journal of Biological Chemistry*, vol. 215, 1976, pp. 4172-4178.

Wallaas, E. , "Fluorescence of Adenine and Inosine Nucleotides", *Acta Chemica Scandinavica*, vol. 17, 1963, pp. 461-463.

Wong, Shan H. , "Chemistry of Protein Conjugation and Crosslinking", *CRC Press*, Boca Raton, FL. 1991.

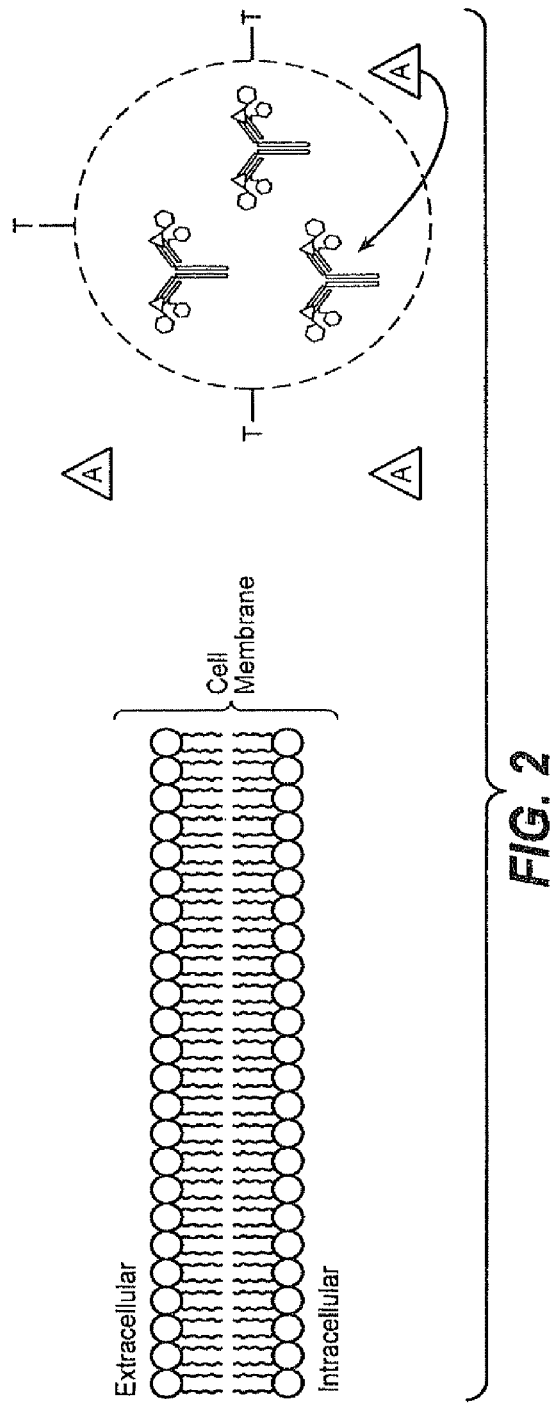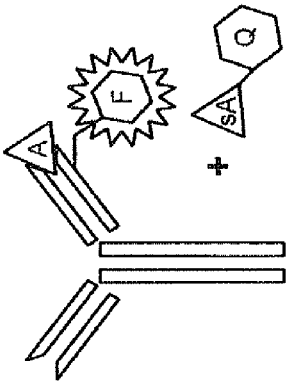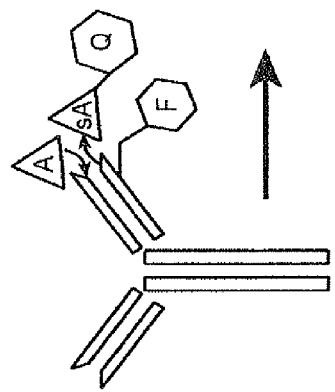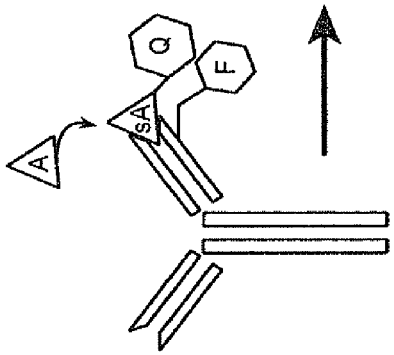
FIG. 2
FIG. 2A
FIG. 2B
FIG. 2C

USE OF ANTIBODY-SURROGATE ANTIGEN SYSTEMS FOR DETECTION OF ANALYTES

1. CROSS REFERENCE TO RELATED APPLICATIONS

This application is a continuation of U.S. application Ser. No. 12/705,746 filed on Feb. 15, 2010, which is a continuation of U.S. application Ser. No. 12/511,948 filed on Jul. 29, 2009, which is a continuation of U.S. application Ser. No. 11/375,825, filed Mar. 15, 2006, which claims benefit under 35 U.S.C. §119(e) to application Ser. No. 60/662,412, filed Mar. 15, 2005, the contents of which are incorporated herein by reference.

2. BACKGROUND

Assays using reporter systems are important tools for studying and detecting analytes in biological and industrial processes. Although numerous approaches have been developed for assaying analytes, there is still a need to find new assay designs that can be used to specifically and conveniently detect and characterize a wide variety of analytes. The development of protein based reporter systems has significantly advanced the art of detection of biological analytes. In spite of these advances, nonspecific labeling of proteins

3. SUMMARY

In one aspect, provided herein are labeling molecules useful for specifically labeling a protein of interest. The proteins are labeled near the binding site of an analyte of interest. The labeling molecules typically comprise a reactive moiety, a label moiety, a target moiety, and a cleavable tether. The reactive moiety is selected such that it is capable of attaching the labeling moiety to the protein. In some embodiments, the reactive moiety comprises a cross-linking group that can form a covalent linkage with a functional group on the protein that is located near the binding site of an analyte of interest. In some embodiments, the reactive moiety comprises a photoreactive group that upon activation by an external energy source is capable of forming a covalent bond with a functional group on the protein.

The label moiety can be any fluorescent entity that is operative in accordance with the various compositions and methods described herein. In some embodiments, the fluorescent moiety comprises at least one fluorescent dye. In some embodiments, the fluorescent moiety comprises at least one rhodamine dye. In some embodiments, the fluorescent moiety comprises two or more fluorescent dyes that can act cooperatively with one another, such as by, for example, fluorescence resonance energy transfer ("FRET").

In some embodiments, the label moiety can be a quenching moiety. The quenching moiety can be any moiety capable of quenching the fluorescence of the fluorescent moiety of a signal molecule when it is in close proximity thereto, such as, for example, by orbital overlap (formation of a ground state dark complex), collisional quenching, FRET, or another mechanism or combination of mechanisms. The quenching moiety can itself be fluorescent, or it can be non-fluorescent. In some embodiments, the quenching moiety comprises a fluorescent dye that has a structural relationship with the fluorescent moiety of the signal molecule such that it quenches the fluorescence of the fluorescent moiety when in close proximity thereto. In such embodiments, selecting a quenching moiety that fluoresces at a wavelength resolvable from that of the fluorescent moiety can provide an internal signal standard to which the fluorescence signal can be referenced The target moiety is capable of binding the labeling molecule to the protein to be labeled. The target moiety can comprise any organic or inorganic molecule capable of binding to a particular position on the protein to be labeled. Non-limiting examples of molecules that can comprise the target moiety include antigens, analytes, enzyme substrates, proteins, carbohydrates, polysaccharides, glycoproteins, hormones, viruses, metabolites, transition state analogs, cofactors, nucleotides, polynucleotide, inhibitors, drugs, nutrients, electrolytes, growth factors and other biomolecules as well as non-biomolecules capable of binding the protein to be labeled.

The cleavable tether connects the target moiety to the label moiety. The cleavable tether comprises at least one cleavable moiety and one or more optional linker moieties. The cleavable moiety comprises at least one functional group that can be cleaved to allow detachment of the target moiety from the protein. The optional linker moieties can be selected to have specified properties. For example, the linker moiety can be hydrophobic or hydrophilic in character, long or short, rigid, semirigid or flexible, depending upon the application. In some embodiments, the linker moieties are selected to increase the solubility of the labeling molecule. In other embodiments, the linker moieties are selected to provide a cleavable tether of a specified length.

The protein can be any protein that can be specifically labeled in close proximity to the analyte binding site and be substantially unlabeled at other positions. Examples of suitable proteins include, but are not limited to, antibodies, enzymes, signal transduction proteins, and receptors.

Labeled proteins can be made by contacting the protein with a labeling molecule comprising a target moiety, a label moiety, a reactive moiety, and a cleavable tether. The target moiety, label moiety, and reactive moiety are connected to one another such that the target moiety can bind the protein, and the reactive moiety can link the labelling molecule to the protein. Agents capable of activating the reactive moiety are added, such that a covalent linkage between the reactive moiety and the protein is formed. The target moiety can be removed by inducing cleavage of the cleavable tether. The resulting labeled proteins can be used in assays to detect analytes of interest.

In another aspect, analyte reporter systems useful for detecting the presence or absence of analytes of interest, i.e., target analytes are provided herein. The analyte reporter systems comprise a labeled protein and a labeled surrogate analyte. The labeled protein can be contacted with the labeled surrogate analyte to form a surrogate analyte-labeled protein complex. In some embodiments, the protein comprises a fluorescent moiety such that upon displacement of the surrogate analyte by a target analyte, an increase in the fluorescence of the fluorescent moiety can be detected.

In some embodiments, the fluorescence of the labeled protein is quenched when the surrogate analyte is bound to the protein. This quenching may be accomplished by a variety of different mechanisms. In some embodiments, the protein and surrogate analyte comprise fluorescent moieties that are capable of "self-quenching" when in close proximity to each other. In other embodiments, quenching can be achieved with the aid of a quenching moiety.

In some embodiments, the surrogate analyte and the labeled protein can be encapsulated in a nanocapsule, liposome, microparticle, lipid particle, vesicles and the like. In some embodiments, the porosity of the membrane comprising the particle used to encapsulate the surrogate analyte and the labeled protein is selected to retain the surrogate analyte-labeled protein complex, and at the same time, allow passage of the target analyte. Thus, the porosity of the particle membrane is such that it allows passage of elements that are less than or equal to 0.5 nm to 5.0 nm in diameter. In some embodiments, the pore diameter of the particles is less than or equal to 5.0 nm. In some embodiments, the pore diameter of the particles is less than or equal to 2.0 nm. In some embodiments, the pore diameter of the particles is less than or equal to 1.5 nm. In some embodiments, the pore diameter of the particles is less than or equal to 1.0 nm. In some embodiments, the pore diameter of the particles is less than or equal to or equal to 0.5 nm.

Also provided are kits for performing methods of the present teachings. For example, in some embodiments, the kits comprise a labeling molecule comprising a target moiety, a label moiety, a reactive moiety, and a cleavable tether. In other embodiments, the kits comprise surrogate analyte-protein complexes useful for detecting the presence of a target analyte. In yet other embodiments, the kits comprise encapsulated surrogate analyte-protein complexes. These and other features of the present teachings are set forth below.

4. BRIEF DESCRIPTION OF THE FIGURES

FIGS. 1A-E provide an exemplary embodiment of an antibody labeling scheme utilizing an exemplary labeling molecule comprising an antigen moiety, a label moiety, a cleavable tether, and a reactive moiety. FIGS. 1A through 1E illustrate an exemplary embodiment of a method of making a functionally labeled antibody 100 with a labeling molecule 110. FIG. 1A illustrates contacting the antibody 100 with a labeling molecule 110 comprising an antigen moiety AgM, a label moiety LM, a reactive moiety RM, and a cleavable tether CT connected to the antigen moiety AgM. As will be appreciated by a person skilled in the art, the arrangement of various moieties illustrated in label molecule 110 provided in FIGS. 1A through 1E is merely exemplary, and the various moieties can be connected to each other in any way that permits them to perform their respective functions. FIG. 1B illustrates contacting the antibody 100 with a labeling molecule 110. FIG. 1C illustrates activating the reactive moiety *RM so as to form a covalent linkage between the activated reactive moiety *RM and the antibody 100. FIG. 1D illustrates cleaving the cleavable tether *CT. FIG. 1E illustrates the cleavage products following cleavage of the cleavable tether, e.g., the labeled antibody and the antigen moiety AgM.

FIG. 2 provides an exemplary embodiment of an intracellular encapsulated analyte reporter system. FIG. 2A illustrates an exemplary surrogate analyte-protein complex wherein the surrogate analyte is a surrogate antigen complexed with a labeled protein, i.e., antibody. In FIG. 2A the antibody is labeled with a fluorescent moiety F and the surrogate antigen sA is labeled with a quenching moiety Q. The labeled F antibody and surrogate antigen sA form a surrogate antigen-antibody complex wherein the quenching moiety Q is positioned so that it is able to quench the fluorescence of the fluorescent moiety F on the antibody. The surrogate antigen-antibody complex is capable of producing a detectable increase in fluorescence upon dissociation of the complex caused by the competitive binding of antigen A to the antibody (FIG. 2B) and the displacement of surrogate antigen sA (FIG. 2C).

Figure 3:
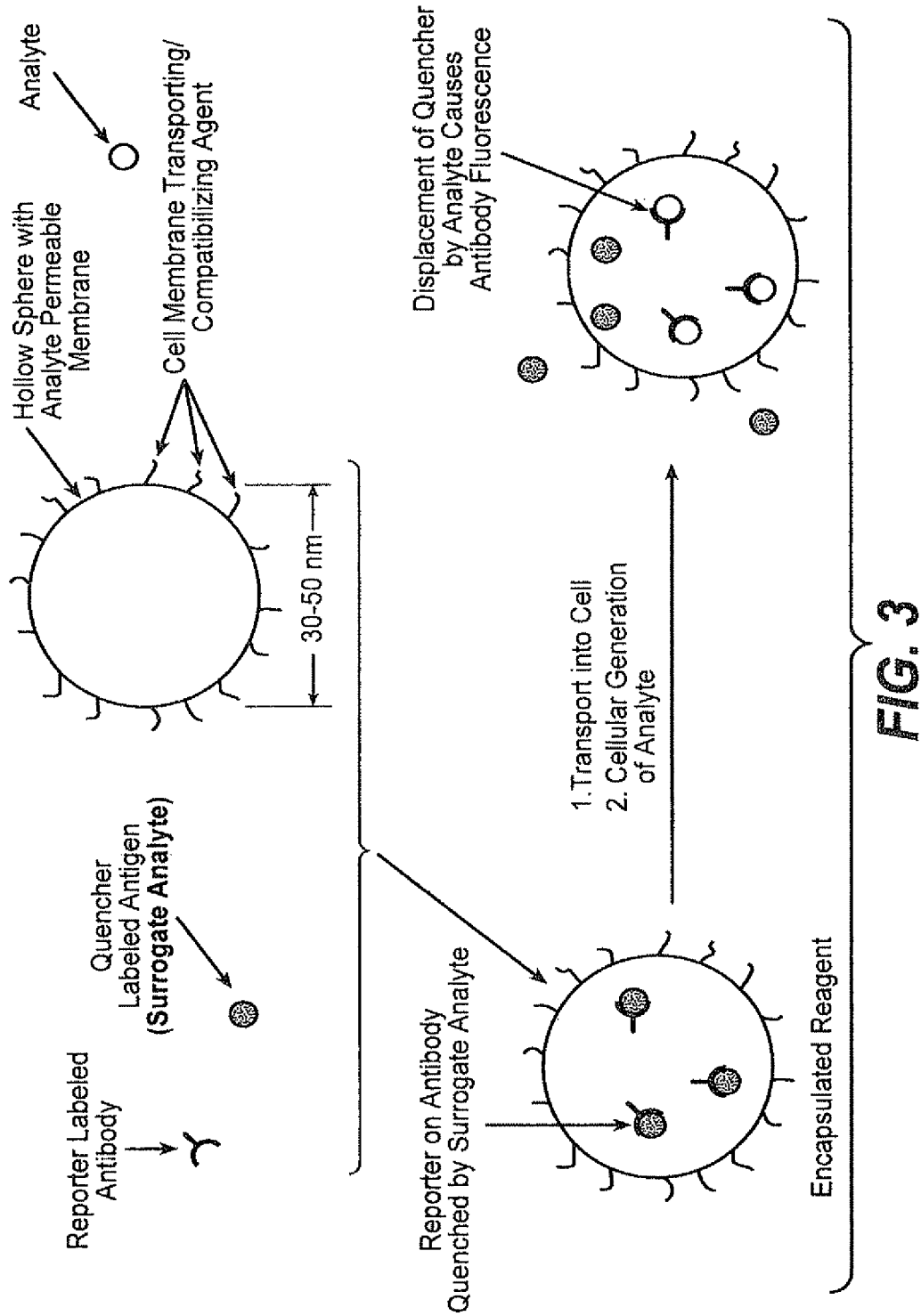

FIG. 3 provides an exemplary embodiment of an analyte reporter system.

5. DETAILED DESCRIPTION

It is to be understood that both the foregoing general description and the following description are exemplary and explanatory only and are not restrictive of the compositions and methods described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting.

5.2 Definitions

As used herein, the following terms and phrases are intended to have the following meanings:

"Antibody" has its standard meaning and is intended to refer to full-length as well antibody fragments, as are known in the art, including Fab, $Fab_2$, single chain antibodies (Fv for example), monoclonal, polyclonal, chimeric antibodies, etc., either produced by the modification of whole antibodies or those synthesized de novo using recombinant DNA technologies.

"Detect" and "detection" have their standard meaning, and are intended to encompass detection, measurement, and characterization of an analyte.

"Protein" has its standard meaning and is intended to refer to proteins, oligopeptides and peptides, derivatives and analogs, including proteins containing non-naturally occurring amino acids and amino acid analogs, and peptidomimetic structures, and includes proteins made using recombinant techniques, i.e. through the expression of a recombinant nucleic acid.

"Quench" has its standard meaning and is intended to refer to a reduction in the fluorescence intensity of a fluorescent group or moiety as measured at a specified wavelength, regardless of the mechanism by which the reduction is achieved. As specific examples, the quenching can be due to molecular collision, energy transfer such as FRET, photoinduced electron transfer such as PET, a change in the fluorescence spectrum (color) of the fluorescent group or moiety or any other mechanism (or combination of mechanisms). The amount of the reduction is not critical and can vary over a broad range. The only requirement is that the reduction be detectable by the detection system being used. Thus, a fluorescence signal is "quenched" if its intensity at a specified wavelength is reduced by any measurable amount. A fluorescence signal is "substantially quenched" if its intensity at a specified wavelength is reduced by at least 50%, for example by 50%, 60%, 70%, 75%, 80%, 85%, 90%, 95%, 96%, 97%, 98%, 99% or even 100%.

5.3 Labeling Molecules

Provided herein are compositions useful for, among other things, specifically labeling a protein. The compositions generally comprise a labeling molecule comprising a target moiety, a label moiety, a reactive moiety, and a cleavable tether. The target moiety is capable of binding the labeling molecule to a protein of interest. The reactive moiety is capable of linking the labeling molecule to the protein. The cleavable tether is capable of being cleaved such that the target moiety is released from the labeling molecule. The labeling molecule can be designed to label virtually any protein of interest, provided that the protein comprises at least one binding domain capable of binding a target moiety. Non-limiting examples of suitable proteins that can be labeled include, but are not limited to, antibodies, enzymes, signal transduction proteins, receptors, as well as fragments of all of the foregoing.

The labeling molecules are useful for specifically labeling a protein of interest, and typically comprise a target moiety, a label moiety, a reactive moiety, and a cleavable tether.

5.3.1 Target Moiety

In some embodiments, the labeling molecule comprises one or more target moiety(ies). The target moiety is capable of binding the labeling molecule to the protein to be labeled. In embodiments, using two or more target moieties, each target moiety can be the same, or some, or all of the target moieties may differ. The target moiety can comprise any organic or inorganic molecule capable of binding the protein to be labeled and capable of containing a cleavable target. Non-limiting examples of molecules that can comprise the target moiety include antigens, analytes, enzyme substrates, proteins, carbohydrates, polysaccharides, glycoproteins, hormones, viruses, metabolites, transition state analogs, cofactors, nucleotides, polynucleotide, inhibitors, drugs, nutrients, growth factors and other biomolecules as well as non-biomolecules capable of binding the protein to be labeled and capable of comprising a cleavable tether.

The specificity and strength of binding between the target moiety and the protein depends in part, on a number of interactions, including, weak, noncovalent bonds, hydrogen bonds, ionic interactions, van der Waals attractions and favorable hydrophobic interactions. The region of the protein that binds with target moiety, referred to herein as the "target binding site", usually consists of a cavity in the protein surface formed by a particular arrangement of amino acids. These amino acids can belong to different portions of the polypeptide chain that come together when the protein folds. Separate regions of the protein surface can provide binding sites for different targets.

The strength with which any two molecules bind to each other can be measured directly. For example, the dissociation constant, $K_d$, can be used to represent the affinity of the protein for the target moiety. In some embodiments, the target moiety and the protein can have a $K_d$ of about $10^{-6}$ or lower. In some embodiments, the dissociation constant can be about $10^{-7}$ or lower. In some embodiments, the dissociation constant can be about $10^{-8}$ or lower. In some embodiments, the dissociation constant can be about $10^{-9}$ or lower. In some embodiments, the dissociation constant can be about $10^{-10}$ or lower. In some embodiments, the dissociation constant can be about $10^{-11}$ or lower.

The composition of the target moiety can depend, in part, on the structure of the analyte to be detected, on the protein being used to detect the target analyte and on the protein to be labeled. For example, if the protein to be labeled is an antibody, the target moiety comprises an antigen comprising at least one epitope recognized by the antibody. As used herein, the term "antigen" refers to an agent that is capable of eliciting the synthesis of a specific antibody in a vertebrate. An "epitope" as used herein refers to an antigenic determinant, e.g., the particular chemical group or groups within an antigen to which a specific antibody binds.

In some embodiments, the target moiety comprises an antigen comprising an epitope for cAMP.

In some embodiments, an enzyme can be labeled using, for example, a target moiety comprising an enzyme substrate, a portion of an enzyme substrate capable of binding the enzyme, a cofactor, a transition state analog, or a small molecule such as a drug. The target moiety can bind the enzyme in any location provided that the labeling moiety is positioned in close proximity to the active site, but does not interfere with the binding of the substrate at the active site, and the analyte binds to the same active site.

In some embodiments, the protein to be labeled can be a receptor. In these embodiments, the target moiety can comprise a ligand, a portion of a ligand capable of binding the receptor, or a small molecule. The target moiety can bind the receptor in any location provided that the labeling moiety is positioned in close proximity to the ligand binding site, but does not interfere with the binding of the ligand by the receptor.

In some embodiments, the protein to be labeled can be a signal transduction protein. In these embodiments, the target moiety can comprise a ligan, a protein of a ligand capable of binding the receptor, or a small molecule involved in a signal transduction pathway. The target moiety can bind the signal transduction protein in any location provided that the labeling moiety is positioned in close proximity to the ligand binding site, but does not interfere with the binding of the ligand by the signal transduction protein.

In some embodiments, the target moiety comprises cAMP and the protein to be labeled comprises a cAMP antibody.

5.3.2 Label Moiety

In some embodiments, the labeling molecule comprises one or more label moiety(ies). In embodiments employing two or more label moieties, each label moiety can be the same, or some, or all, of the label moieties may differ.

In some embodiments, the label moiety comprises a fluorescent moiety. The fluorescent moiety can comprise any entity that provides a fluorescent signal and that can be used in accordance with the methods and principles described herein. Typically, the fluorescent moiety of the labeling molecule comprises a fluorescent dye that in turn comprises a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, such as xanthenes, rhodamines, fluoresceins, cyanines, phthalocyanines, squaraines, bodipy dyes, coumarins, oxazines, and carbopyronines.

In some embodiments, the fluorescent moiety comprises a xanthene dye. Generally, xanthene dyes are characterized by three main features: (1) a parent xanthene ring; (2) an exocyclic hydroxyl or amine substituent; and (3) an exocyclic oxo or imminium substituent. The exocyclic substituents are typically positioned at the C3 and C6 carbons of the parent xanthene ring, although "extended" xanthenes in which the parent xanthene ring comprises a benzo group fused to either or both of the C5/C6 and C3/C4 carbons are also known. In these extended xanthenes, the characteristic exocyclic substituents are positioned at the corresponding positions of the extended xanthene ring. Thus, as used herein, a "xanthene dye" generally comprises one of the following parent rings:

—$SR^a$, —$NR^aR^a$, perhalo ($C_1$-$C_6$) alkyl, —$CX_3$, —$CF_3$, —CN, —OCN, —SCN, —NCO, —NCS, —NO, —$NO_2$, —$N_3$, —$S(O)_2O^-$, —$S(O)_2OH$, —$S(O)_2R^a$, —C(O)R, —C(O)X, —$C(S)R^a$, —C(S)X, —$C(O)OR^a$, —$C(O)O^-$, —$C(S)OR^a$, —$C(O)SR^a$, —$C(S)SR^a$, —$C(O)NR^aR^a$, —$C(S)NR^aR^a$ and —$C(NR)NR^aR^a$, where each X is independently a halogen (preferably —F or —Cl) and each $R^a$ is independently hydrogen, ($C_1$-$C_6$) alkyl, ($C_1$-$C_6$) alkanyl, ($C_1$-$C_6$) alkenyl, ($C_1$-$C_6$) alkynyl, ($C_5$-$C_{20}$) aryl, ($C_6$-$C_{26}$) arylalkyl, ($C_5$-$C_{20}$) arylaryl, 5-20 membered heteroaryl, 6-26 membered heteroarylalkyl, 5-20 membered heteroaryl-heteroaryl, carboxyl, acetyl, sulfonyl, sulfinyl, sulfone, phosphate, or phosphonate. Generally, substituents which do not tend to completely quench the fluorescence of the parent ring are preferred, but in some embodiments quenching substituents may be desirable. Substituents that tend to quench fluorescence of parent xanthene rings comprise heavy atoms, such as —$NO_2$, —Br and —I, and/or other functional moieties, such as $NO_2$.

The C1 and C2 substituents and/or the C7 and C8 substituents can be taken together to form substituted or unsubstituted buta[1,3]dieno or ($C_5$-$C_{20}$) aryleno bridges. For purposes of illustration, exemplary parent xanthene rings including unsubstituted benzo bridges fused to the C1/C2 and C7/C8 carbons are illustrated below:

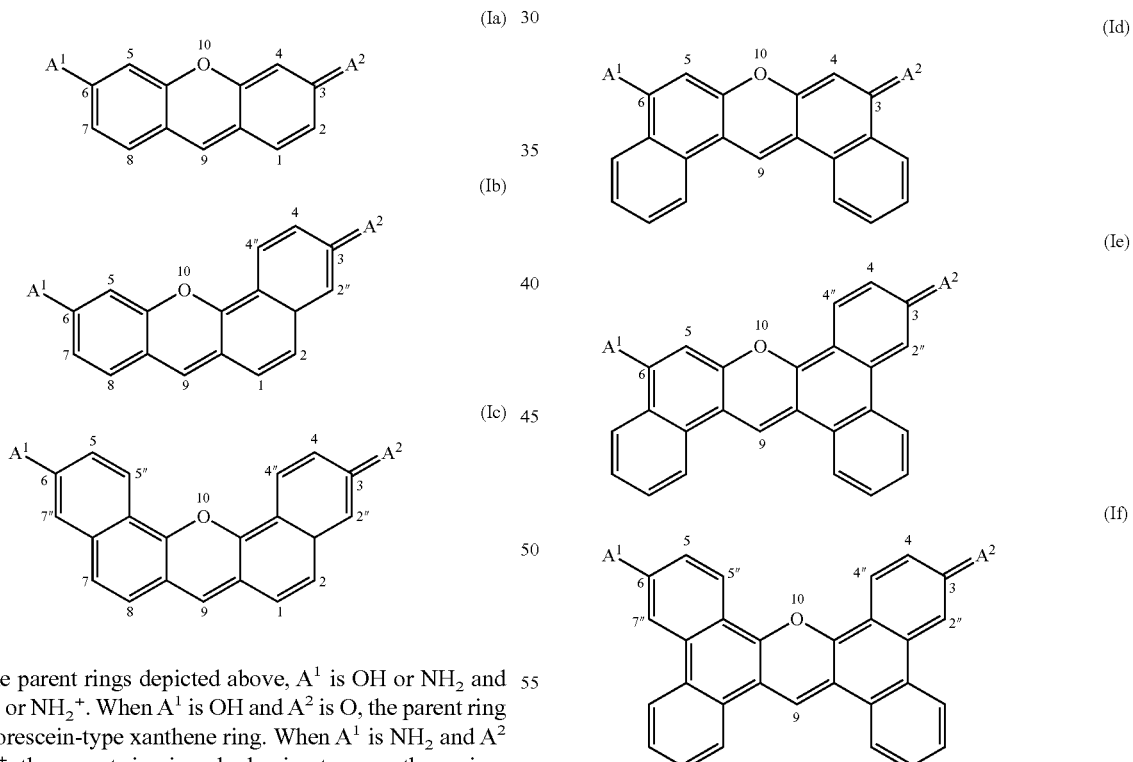

In the parent rings depicted above, $A^1$ is OH or $NH_2$ and $A^2$ is O or $NH_2^+$. When $A^1$ is OH and $A^2$ is O, the parent ring is a fluorescein-type xanthene ring. When $A^1$ is $NH_2$ and $A^2$ is $NH_2^+$, the parent ring is a rhodamine-type xanthene ring. When $A^1$ is $NH_2$ and $A^2$ is O, the parent ring is a rhodol-type xanthene ring.

One or both of nitrogens of $A^1$ and $A^2$ (when present) and/or one or more of the carbon atoms at positions C1, C2, C2", C4, C4", C5, C5", C7", C7 and C8 can be independently substituted with a wide variety of the same or different substituents. In one embodiment, typical substituents comprise, but are not limited to, —X, —$R^a$, —$OR^a$, The benzo or aryleno bridges may be substituted at one or more positions with a variety of different substituent groups, such as the substituent groups previously described above for carbons C1-C8 in structures (Ia)-(Ic), supra. In embodiments including a plurality of substituents, the substituents may all be the same, or some or all of the substituents can differ from one another.

When $A^1$ is $NH_2$ and/or $A^2$ is $NH_2^+$, the nitrogen atoms may be included in one or two bridges involving adjacent carbon atom(s). The bridging groups may be the same or different, and are typically selected from ($C_1$-$C_{12}$) alkyldiyl, ($C_1$-$C_{12}$) alkyleno, 2-12 membered heteroalkyldiyl and/or 2-12 membered heteroalkyleno bridges. Non-limiting exemplary parent rings that comprise bridges involving the exocyclic nitrogens are illustrated below:

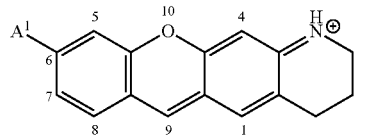 (Ig)

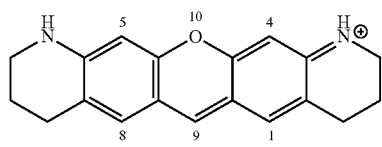 (Ih)

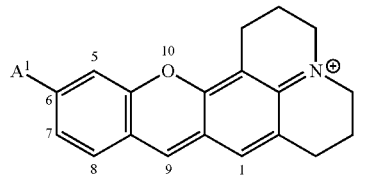 (Ii)

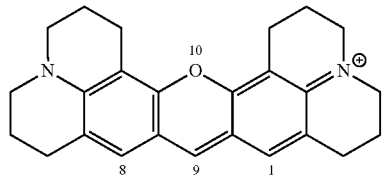 (Ij)

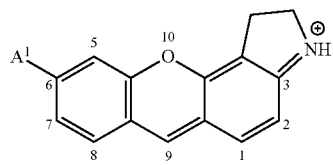 (Ik)

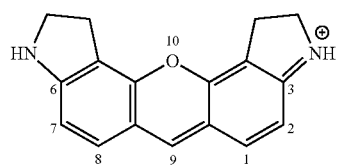 (Il)

The parent ring may also comprise a substituent at the C9 position. In some embodiments, the C9 substituent is selected from acetylene, lower (e.g., from 1 to 6 carbon atoms) alkanyl, lower alkenyl, cyano, aryl, phenyl, heteroaryl, and substituted forms of any of the preceding groups. In embodiments in which the parent ring comprises benzo or aryleno bridges fused to the C1/C2 and C7/C8 positions, such as, for example, rings (Id), (Ie) and (If) illustrated above, the C9 carbon is preferably unsubstituted.

In some embodiments, the C9 substituent is a substituted or unsubstituted phenyl ring such that the xanthene dye comprises one of the following structures:

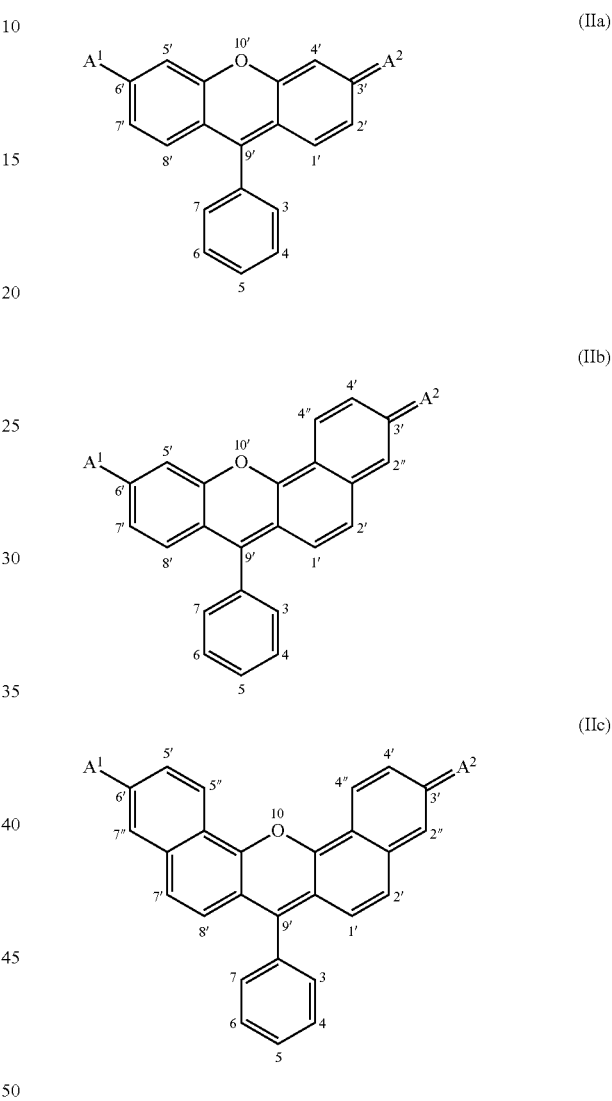

The carbons at positions 3, 4, 5, 6 and 7 may be substituted with a variety of different substituent groups, such as the substituent groups previously described for carbons C1-C8. In some embodiments, the carbon at position C3 is substituted with a carboxyl (—COOH) or sulfuric acid (—$SO_3H$) group, or an anion thereof. Dyes of formulae (IIa), (IIb) and (IIc) in which $A^1$ is OH and $A^2$ is O are referred to herein as fluorescein dyes; dyes of formulae (IIa), (IIb) and (IIc) in which $A^1$ is $NH_2$ and $A^2$ is $NH_2^+$ are referred to herein as rhodamine dyes; and dyes of formulae (IIa), (IIb) and (IIc) in which $A^1$ is OH and $A^2$ is $NH_2^+$ (or in which $A^1$ is $NH_2$ and $A^2$ is O) are referred to herein as rhodol dyes.

As highlighted by the above structures, when xanthene rings (or extended xanthene rings) are included in fluorescein, rhodamine and rhodol dyes, their carbon atoms are numbered differently. Specifically, their carbon atom numberings include primes. Although the above numbering systems for fluorescein, rhodamine and rhodol dyes are provided for convenience, it is to be understood that other numbering systems may be employed, and that they are not intended to be limiting. It is also to be understood that while one isomeric form of the dyes are illustrated, they may exist in other isomeric forms, including, by way of example and not limitation, other tautomeric forms or geometric forms. As a specific example, carboxy rhodamine and fluorescein dyes may exist in a lactone form.

In some embodiments, the fluorescent moiety comprises a rhodamine dye. Exemplary suitable rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichloro-tetramethylrhodamine (dTAMRA). Additional suitable rhodamine dyes include, for example, those described in U.S. Pat. Nos. 6,248,884, 6,111,116, 6,080,852, 6,051,719, 6,025,505, 6,017,712, 5,936,087, 5,847,162, 5,840,999, 5,750,409, 5,366,860, 5,231,191, and 5,227,487; PCT Publications WO 97/36960 and WO 99/27020; Lee et al., NUCL. ACIDS RES. 20:2471-2483 (1992), Arden-Jacob, NEUE LANWELLIGE XANTHEN-FARBSTOFFE FÜR FLUORESZENZSONDEN UND FARBSTOFF LASER, Verlag Shaker, Germany (1993), Sauer et al., J. FLUORESCENCE 5:247-261 (1995), Lee et al., NUCL. ACIDS RES. 25:2816-2822 (1997), and Rosenblum et al., NUCL. ACIDS RES. 25:4500-4504 (1997). A particularly preferred subset of rhodamine dyes are 4,7-dichlororhodamines. In one embodiment, the fluorescent moiety comprises a 4,7-dichloro-orthocarboxyrhodamine dye.

In some embodiments, the fluorescent moiety comprises a fluorescein dye. Exemplary suitable fluorescein include, but are not limited to, fluorescein dyes described in U.S. Pat. Nos. 6,008,379, 5,840,999, 5,750,409, 5,654,442, 5,188,934, 5,066,580, 4,933,471, 4,481,136 and 4,439,356; PCT Publication WO 99/16832, and EPO Publication 050684. A preferred subset of fluorescein dyes are 4,7-dichlorofluoresceins. Other preferred fluorescein dyes include, but are not limited to, 5-carboxyfluorescein (5-FAM) and 6-carboxyfluorescein (6-FAM). In one embodiment, the fluorescein moiety comprises a 4,7-dichloro-orthocarboxyfluorescein dye.

In some embodiments, the fluorescent moiety can include a cyanine, a phthalocyanine, a squaraine, or a bodipy dye, such as those described in the following references and the references cited therein: U.S. Pat. Nos. 6,080,868, 6,005,113, 5,945,526, 5,863,753, 5,863,727, 5,800,996, and 5,436,134; and PCT Publication WO 96/04405.

In some embodiments, the fluorescent moiety can comprise a network of dyes that operate cooperatively with one another such as, for example by FRET or another mechanism, to provide large Stoke's shifts. Such dye networks typically comprise a fluorescence donor moiety and a fluorescence acceptor moiety, and may comprise additional moieties that act as both fluorescence acceptors and donors. The fluorescence donor and acceptor moieties can comprise any of the previously described dyes, provided that dyes are selected that can act cooperatively with one another. In a specific embodiment, the fluorescent moiety comprises a fluorescence donor moiety which comprises a fluorescein dye and a fluorescence acceptor moiety which comprises a fluorescein or rhodamine dye. Non-limiting examples of suitable dye pairs or networks are described in U.S. Pat. Nos. 6,399,392, 6,232,075, 5,863,727, and 5,800,996.

In some embodiments, the label moiety comprises a quenching moiety. The quenching moiety can be any moiety capable of quenching the fluorescence of a fluorescent moiety when it is in close proximity thereto, such as, for example, by orbital overlap (formation of a ground state dark complex), collisional quenching, FRET, or another mechanism or combination of mechanisms. The quenching moiety can itself be fluorescent, or it can be non-fluorescent. In some embodiments, the quenching moiety comprises a fluorescent dye that has an absorbance spectrum that sufficiently overlaps the emissions spectrum of a fluorescent moiety such that it quenches the fluorescence of the fluorescent moiety when in close proximity thereto.

5.3.3 Reactive Moiety

In some embodiments, the labeling molecule comprises one or more reactive moiety(ies). The reactive moiety can be used to attach the label moiety to the protein near a target binding site. The reactive moiety may be attached directly, or indirectly via one or more optional linkers to the label moiety. The reactive moiety can comprise any reactive group that is capable of forming a covalent linkage with a corresponding reactive group on the protein. Thus, the reactive moiety can comprise any reactive group known in the art, so long as it is compatible with the methods and compositions described herein. In embodiments employing two or more reactive moieties, each reactive moiety can be the same, or some or all of the reactive moieties may differ.

In some embodiments, the reactive moiety comprises a cross-linker, i.e., a cross-linking group. Cross-linker reactivity, specificity, and solubility characteristics are well known in the art. Guidance for selecting appropriate cross-linking agents can be found in Mattson et al., MOL BIOL REP. April; 17(3):167-83 (1993), Double-Agents™ Cross-linking reagents, Selection Guide, Pierce Biotechnology Inc., 2003). See also, Wong, 1993, Chemistry of Protein Conjugation and Cross-linking, CRC Press, Boca Raton.

In some embodiments, the reactive moiety comprises a functional group that can be used to attach the reactive moiety to the protein by forming a covalent linkage with a complementary group present on the protein. Pairs of complementary groups capable of forming covalent linkages are well known. In some embodiments, the protein comprises a nucleophilic group and the cross-linking group comprises an electrophilic group. In other embodiments, the cross-linking group comprises a nucleophilic group and the protein comprises an electrophilic group. "Complementary" nucleophilic and electrophilic groups (or precursors thereof that can be suitable activated) useful for effecting linkages stable to biological and other assay conditions are well known and can be used. Examples of suitable complementary nucleophilic and electrophilic groups, as well as the resultant linkages formed therefrom, are provided in Table 1.

TABLE 1

| Electrophilic Group | Nucleophilic Group | Resultant Covalent Linkage |
|---|---|---|
| activated esters* | amines/anilines | Carboxamides |
| acyl azides** | amines/anilines | Carboxamides |
| acyl halides | amines/anilines | Carboxamides |
| acyl halides | alcohols/phenols | Esters |
| acyl nitriles | alcohols/phenols | Esters |
| acyl nitriles | amines/anilines | Carboxamides |
| aldehydes | amines/anilines | Imines |
| aldehydes or ketones | hydrazines | Hydrazones |
| aldehydes or ketones | hydroxylamines | Oximes |
| Alkyl halides | amines/anilines | alkyl amines |
| Alkyl halides | carboxylic acids | Esters |
| Alkyl halides | thiols | Thioethers |
| Alkyl halides | alcohols/phenols | Ethers |
| Alkyl sulfonates | thiols | Thioethers |
| Alkyl sulfonates | carboxylic acids | Esters |
| Alkyl sulfonates | alcohols/phenols | Esters |
| anhydrides | alcohols/phenols | Esters |
| anhydrides | amines/anilines | Caroboxamides |
| aryl halides | thiols | Thiophenols |
| aryl halides | amines | aryl amines |
| aziridines | thiols | Thioethers |
| boronates | glycols | boronate esters |
| carboxylic acids | amines/anilines | Carboxamides |
| carboxylic acids | alcohols | Esters |
| carboxylic acids | hydrazines | Hydrazides |
| carbodiimides | carboxylic acids | N-acylureas or anhydrides |
| diazoalkanes | carboxylic acids | Esters |
| epoxides | thiols | Thioethers |
| haloacetamides | thiols | Thioethers |
| halotriazines | amines/anilines | Aminotriazines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | Phosphate esters |
| silyl halides | Alcohols | silyl ethers |
| sulfonate esters | amines/anilines | alkyl amines |
| sulfonate esters | Thiols | Thioethers |
| sulfonate esters | carboxylic acids | Esters |
| sulfonate esters | Alcohols | Esters |
| sulfonyl halides | amines/anilines | Sulfonamides |
| sulfonyl halides | phenols/alcohols | sulfonate esters |
| Diazonium salt | aryl | Azo |

*Activated esters, as understood in the art, generally have the formula —C(O)Z, where Z is a good leaving group (e.g., oxysuccinimidyl, oxysulfosuccinimidyl, 1-oxybenzotriazolyl, etc.).
**Acyl azides can rearrange to isocyanates.

In some embodiments, the reactive moiety comprises a cross-linker comprising a photoreactive group. A photoreactive group has at least one latent photoreactive group that upon activation by an external energy source, forms covalent bonds with other molecules. See, e.g., U.S. Pat. No. 5,002,582, the disclosure of which is incorporated herein by reference. For example, upon exposure to a suitable light source, the photoreactive group can be activated to form a covalent bond with an adjacent chemical structure e.g. an aliphatic carbon-hydrogen bond.

Suitable photoreactive groups include, for example, azides, diazos, diazirines, aromatic ketones, and quinones. Exemplary photoreactive groups, and their residues upon activation, are shown in Table 2.

TABLE 2

| Photoreactive Group | Residue Functionality |
|---|---|
| aryl azides | amine R—NH—R' |
| acyl azides | amide R—CO—NH—R' |
| azidoformates | carbamate WO—CO—NH—R' |

TABLE 2-continued

| Photoreactive Group | Residue Functionality |
|---|---|
| sulfonyl azides | sulfonamide R—SO$_2$—NH—R' |
| phosphoryl azides | phosphoramide (RO)$_2$ PO—NH—R' |
| diazoalkanes | new C—C bond |
| diazoketones | new C—C bond and ketone |
| diazoacetates | new C—C bond and ester |
| beta-keto-alpha-diazoacetates | new C—C bond and beta-ketoester |
| aliphatic azo | new C—C bond |
| diazirines | new C—C bond |
| ketenes | new C—C bond |
| photoactivated ketones | new C—C bond and alcohol |

In some embodiments, the photoreactive group comprises an aryl ketone, such as, acetophenone, anthraquinone, anthrone and anthrone-like heterocycles (i.e., heterocyclic analogues of anthrone such as those having N, O, or S in the 10-position), or their substituted (e.g., ring substituted) derivatives, benzophenone, benzophenone maleimido, succinimidyl ester of 4-benzoylbenzoic acid.

The functional groups of some aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased linking efficiency.

In some embodiments the photoreactive group comprises an azide, and includes arylazides (C$_6$R$_5$N$_3$) such as phenyl azide, 4-fluoro-3-nitrophenyl azide, acyl azides (—CO—N$_3$) such as ethyl azidoformiate, phenyl azidoformate, sulfonyl azides (—SO$_2$—N$_3$) such as benzenesulfonyl azide, and phosphoryl azides (RO)$_2$PON$_3$ such as diphenyl phosphoryl azide and diethyl phosphoryl azide.

In some embodiments, the photoreactive group comprises a diazo compounds, and includes diazoalkanes (—CHN$_2$) such as diazomethane and diphenyldiazomethane, diazoketones (—CO—CHN$_2$) such as diazoacetophenone and 1-trifluoromethyl-1-diazo-2-pentanone, diazoacetates (—CO—CN$_2$—CO—O—) such as t-butyl alpha diazoacetoacetate.

Other suitable photoreactive groups include aliphatic azo compounds such as azobisisobutyronitrile, diazirines (—CHN$_2$) such as 3-trifluoromethyl-3-phenyldiazirine and ketenes (—CH=C=O) such as ketene and diphenylketene, and photoreactive groups including quinone such as, for example anthraquinone.

Additional examples of suitable activatable reactive moieties, includes, but are not limited to, molecules that can be activated by pH, heat, or electrochemically such as peroxide.

In some embodiments, the reactive moiety comprises a chemical group activated by a change in pH. Chemical groups activated by a change in pH are well known and can be used in forming covalent bonds. (see, e.g., Double-Agents™ Cross-linking reagents, Selection Guide, Pierce Biotechnology Inc., 2003). Suitable non-limiting examples include imidoesters, maleimide groups, iodoacetyl group, and glyoxals.

Imidoesters can react with primary amines to form amidine bonds at about pH 8-10. N-Hydroxysuccinimide-Esters (NHS-Esters) can react with primary amines at physiological pH. The accessible α-amine groups present on the N-termini of proteins and ε-amines on lysine residues react with NHS-esters and form amide bonds. Maleimide groups can react specifically with sulfhydryl groups when the pH of the reaction mixture is between pH 6.5 and 7.5 and forms a stable thioether linkage. At neutral pH, maleimides can react with sulfhydryls 1.000-fold faster than with amines, but at pH>8.5, the reaction favors primary amines. Iodoacetyl group can react with sulfhydryl groups at physiological pH. The reaction of the iodoacetyl group with a sulfhydryl proceeds by nucleophilic substitution of iodine with a thiol producing a stable thioether linkage. Iodoacetyl groups can react with imidazoles at a pH of about pH 6.9-7.0. Glyoxals can target arginines at mildly alkaline pH. Glyoxals are useful compounds for targeting the guanidinyl portion of arginine residues. There can be cross-reactivity with lysines at about pH 9.

In some embodiments, the reactive moiety comprises a chemical group that can be activated by heat. Chemical groups that can be activated by heat are well known by those skilled in the art. Suitable non-limiting examples of chemical groups that can be activated by heat include peroxides, e.g., benzoyl peroxide, and azo groups, e.g., azobisisobutyronitriles.

In some embodiments, the reactive moiety comprises a chemical group that can be activated electrochemically. Chemical groups that can be activated electrochemically are well known by those skilled in the art. Suitable non-limiting examples of chemical groups that can be activated electrochemically include halobenzyl compounds, such as α-bromotoluene, and organometallic compounds, such as phenyl mercury compounds.

In some embodiments, a linker moiety can be inserted between the reactive groups to minimize steric interference with the activity of the protein. The chemical composition of the linker moiety is not critical. Any type of linker that permits the resultant labeled protein to function as described herein can be used. Suitable linker moieties are described below.

5.3.4 Cleavable Tether

In some embodiments, the labeling molecule comprises a cleavable tether. Generally, the cleavable tether connects the target moiety to the label moiety. The cleavable tether comprises at least one cleavable moiety and one or more optional linker moieties. The cleavable moiety comprises at least one functional group that can be cleaved to allow detachment of the target moiety from the protein. The optional linker moieties typically comprise one or more linkage groups that can be used to affect the solubility of the labeling molecule and/or that function to link the cleavable tether to the target moiety and the label moiety.

The cleavable moiety can comprise any number of functional groups. For example, the cleavable moiety can comprise a functional group that can be cleaved by a selected cleaving agent when the cleavable tether is bound to, or interacting with, the labeled protein. As another example, the cleavable moiety can comprises a functional group that can be cleaved under selected cleaving conditions, or by a selected chemical reaction. Thus, cleavable moieties can include functional groups that can be photolytically, chemically, thermally or enzymatically cleaved. See, e.g., U.S. Pat. No. 5,721,099, U.S. Pat. Pub. No. 2004/0166529, and Greene et al., PROTECTIVE GROUPS IN ORGANIC SYNTHESIS, 2nd ed. Wiley, 1991, and U.S. patent application Ser. No. 10/828, 647.

In some embodiments, the cleavable moiety comprises silyl groups that can be cleaved with halogens, such as fluoride, bromine or chlorine, by oxidation or acid.

In other embodiments, the cleavable moiety can comprise photolabile linkages, such as o-nitrobenzyl, 7-nitroindanyl, 2-nitrobenzhydryl ethers or esters, etc., that can be cleaved with electromagnetic radiation.

Other examples of cleavable moieties are known to those skilled in the art. For example, catechols, which can be cleaved with cerium salts, can be used as cleavable moieties. Olefins, which can be cleaved with ozone, permanganate or osmium tetroxide, can be used as cleavable moieties. Sulfides, which can be cleaved with singlet oxygen or by enzyme catalyzed oxidative cleavage with hydrogen peroxide, where the resulting sulfone can undergo elimination, can be used as cleavable moieties. Furans, which can be cleaved with oxygen or bromine in methanol, can be used as cleavable moieties. Tertiary alcohols ketals and acetals, which can be cleaved with acid, can be used as cleavable moieties. Alpha- and beta-substituted ethers and esters, which can be cleaved with base, where the substituent is an electron withdrawing group, e.g., sulfone, sulfoxide, ketone, etc., and the like, can be used as cleavable moieties. Substituted benzyl ether or derivatives thereof, e.g. benzhydryl ether, indanyl ether, etc., which may be cleaved by acidic or mild reductive conditions, can be used as cleavable moieties.

In some embodiments, two or more cleavable moieties are used. In these embodiments, each cleavable moiety can be the same, or some, or all, of the cleavable moieties may differ.

In some embodiments, the cleavable tether comprises one or more optional linker moieties. The linker moieties can comprise any linkage group capable of connecting the cleavable moiety to another moiety in the labeling molecule. In embodiments employing two or more linker moieties, each of the linker moieties can be the same, or some, or all, of the linker moieties may differ.

In some embodiments, the linker moiety comprises one or more (bis)ethylene glycol group(s). As will be appreciated by a person skilled in the art, the number of oxyethylene units comprising the linker moiety can be selectively varied. For example, one, two, three or more oxyethylene units may be used to form a linker moiety. Virtually any combination of the same or different oxyethylene units that permits the cleavable tether to function as described herein may be used. In a specific example, the linker moiety may comprise from 1 to about 5 of the same or different lower oxyethylene units (e.g., —$(CH_2)_xCH_2$—), where x is an integer ranging from 0 to 6). The chemical composition of the linker moiety is not critical. Any type of linker moiety that permits the resultant labeling molecule to function as described herein can be used.

A linker moiety can be selected to have specified properties. For example, the linker moiety can be hydrophobic in character, hydrophilic in character, long or short, rigid, semirigid or flexible, depending upon the particular application. The linker moiety can be optionally substituted with one or more substituents or one or more linking groups for the attachment of additional substituents, which may be the same or different, thereby providing a "polyvalent" linking moiety capable of conjugating or linking additional molecules or substances to the labeling molecule. In certain embodiments, however, the linker moiety does not comprise such additional substituents or linking groups.

A wide variety of linker moieties comprised of stable bonds are known in the art, and include by way of example and not limitation, alkyldiyls, substituted alkyldiyls, alkylenos (e.g., alkanos), substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryl diyls, substituted heteroaryl-heteroaryl diyls, heteroarylalkyldiyls, substituted heteroarylalkyldiyls, heteroaryl-heteroalkyldiyls, substituted heteroaryl-heteroalkyldiyls, and the like. Thus, a linker moiety can include single, double, triple or aromatic carbon-carbon bonds, nitrogen-nitrogen bonds, carbon-nitrogen bonds, carbon-oxygen bonds, carbon-sulfur bonds and combinations of such bonds, and may therefore include functionalities such as carbonyls, ethers, thioethers, carboxamides, sulfonamides, ureas, urethanes, hydrazines, etc. In some embodiments, the linker moiety has from 1-20 non-hydrogen atoms selected from the group consisting of C, N, O, P, and S and is composed of any combination of ether, thioether, amine, ester, carboxamide, sulfonamides, hydrazide, aromatic and heteroaromatic groups.

Choosing a linker moiety having properties suitable for a particular application is within the capabilities of those having skill in the art. For example, where a rigid linker moiety is desired, the linker moiety may comprise a rigid polypeptide such as polyproline, a rigid polyunsaturated alkyldiyl or an aryldiyl, biaryldiyl, arylaryldiyl, arylalkyldiyl, heteroaryldiyl, biheteroaryldiyl, heteroarylalkyldiyl, heteroaryl-heteroaryldiyl, etc. Where a flexible linker moiety is desired, the linker moiety may comprise a flexible polypeptide such as polyglycine or a flexible saturated alkanyldiyl or heteroalkanyldiyl. Hydrophilic linker moieties may comprise, for example, polyalcohols, polyethers, such as polyalkyleneglycols, or polyelectroyles, such as polyquaternary amines. Hydrophobic linker moieties may comprise, for example, alkyldiyls or aryldiyls.

In some embodiments, the linker moiety comprises a peptide bond. Skilled artisans will appreciate that while using peptide bonds may be convenient, the various moieties comprising the labeling molecule can be linked to one another via any linkage that is stable to the conditions under which the labeling molecule will be used.

In some embodiments, the cleavable tether comprises the structure:

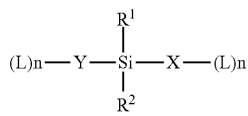

wherein:
Y and/or X is an oxygen atom,
$R^1$ and $R^2$ are hydrocarbons;
L represents optional linker moieties; and
n is an integer from 0 to 5.

In the embodiment illustrated above, when Y or X is an oxygen atom, the other moiety can comprise an oxygen atom or a carbon atom. For example, when Y is an oxygen atom, X can be a carbon atom. As another example, when X is an oxygen atom, Y can be a carbon atom. In yet another example, both Y and X can be oxygen atoms.

In some embodiments, the cleavable tether comprises the structure:

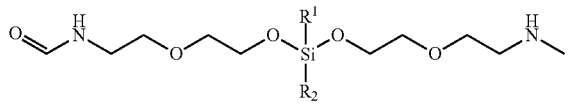

wherein $R^1$ and $R^2$ are hydrocarbons.

The cleavable tether can be of any length provided, that upon cleavage of the cleavable moiety, the labeling moiety is positioned in close proximity to the analyte binding site at a location that does not interfere with target binding. Choosing a cleavable tether having properties suitable for a particular application is within the capabilities of those having skill in the art. For example, competitive binding assays can be performed with proteins labeled with labeling molecules comprising cleavable tethers of various lengths to determine the optimal length of the cleavable tether such that the label moiety does not substantially interfere with target binding.

In some embodiments the cleavable tether can be from 5 to about 20 Angstroms.

The various moieties comprising the labeling molecule can be connected to each other in any way that permits them to perform their respective functions. In some, embodiments the target moiety, label moiety, reactive moiety, and cleavable tether can be directly linked to each other i.e., covalently linked to each other. In some, embodiments, one, some, or all of the moieties can be connected indirectly to one another, i.e., via one or more optional linkers. Any of the linkers previously described can be used to link the various moieties to one another.

In some embodiments, the cleavable tether can be linked directly to the target moiety. In some embodiments, the cleavable tether can be linked indirectly to the target moiety via an optional linker. In some embodiments, the cleavable tether is linked directly to the label moiety. In some embodiments, the cleavable tether is linked indirectly to the label moiety via an optional linker. In some embodiments, the cleavable tether is linked directly to the reactive moiety. In some embodiments, the cleavable tether is linked indirectly to the reactive moiety via an optional linker.

In some embodiments, the target moiety, label moiety, reactive moiety, and cleavable tether can be linked to one another via a multivalent linker. Multivalent linkers can be any molecule having two, three, four, or more attachment sites suitable for attaching other molecules and moieties thereto, or that can be appropriately activated to attach other molecules and moieties thereto. For example, the backbone of the linker to which the reactive (or activatable) linking groups are attached could be a linear, branched or cyclic saturated or unsaturated alkyl, a mono or polycyclic aryl or an arylalkyl. The linker need not be limited to carbon and hydrogen atoms. Indeed, the linker can comprise single, double, triple or aromatic carbon-carbon bonds, carbon-nitrogen bonds, nitrogen-nitrogen bonds, carbon-oxygen bonds, carbon-sulfur bonds, phosphorus-oxygen bonds, and combinations thereof, and therefore can comprise functionalities such as carbonyls, ethers, thioethers, carboxamides, sulfonamides, ureas, urethanes, hydrazines, etc.

The functional groups on the multivalent linker can be any member of a pair of complementary reactive groups capable of forming covalent linkages. In some embodiments, each reactive group comprising the multifunctional linker is an electrophilic group or a nucleophilic group that is capable of reacting with a complementary nucleophilic group or electrophilic group to form a covalent linkage stable to biological assay conditions The reactive groups on the multivalent linker may all be the same, or some or all of them may be different. In some embodiments, reactive groups are selected that have different chemical reactivities to facilitate the selective attachment of the various moieties described herein, to the linker.

In some embodiments the multivalent linker can be a trifunctional linker. In some embodiments, the trifunctional linker is an amino acid, which may be an alpha amino acid, a beta amino acid, a gamma amino or other type of amino acid that comprises a side chain having a suitable reactive functional group. Specific examples of suitable amino acids comprise, but are not limited to, lysine, glutamate, cysteine, serine, homoserine and 1,3-diaminobutyric acid. These amino acids may be in either the D- or L-configuration, or may constitute racemic or other mixtures thereof.

In some embodiments, the labeling molecule comprises the structure:

$$TM\text{-}(L^1)_n\text{-}CT\text{-}(L^2)_n\text{-}LM\text{-}(L^3)_n\text{-}RM$$

wherein:
TM represents the target moiety;
CT represents the cleavable tether;
LM represents the label moiety;
RM represents the reactive moiety;
$L^1$-$L^3$ represents optional linkers; and
n is an integer form 0 to 5

$L^1$, $L^2$, and $L^3$ can comprise any of the optional linkers discussed above. In some embodiments, the linkers can be the same. In some embodiments, the linkers can be different. In some embodiments, some of the linkers can be the same and others different.

In some embodiments, the labeling molecule comprises the structure:

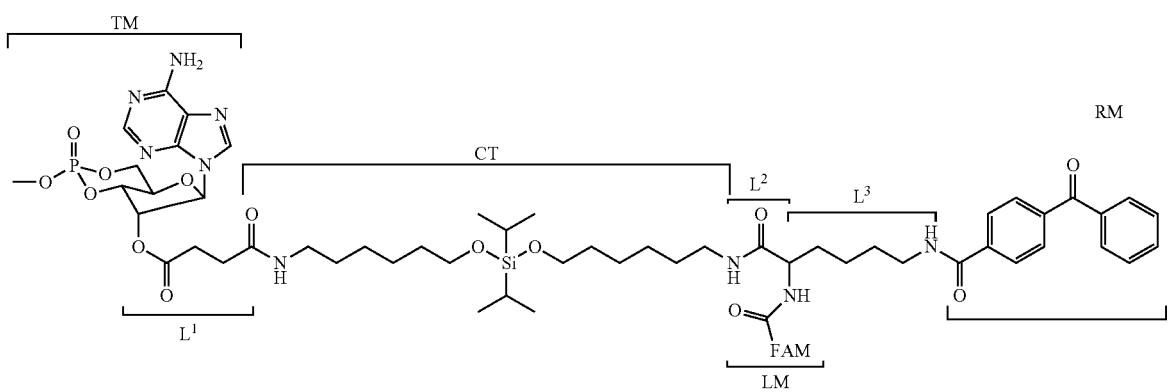

wherein:
TM represents the target moiety, comprising a cAMP antigen;
CT represents the cleavable tether, comprising silyl cleavable moiety and two optional alkyl linkers;
LM represents the label moiety comprising a carboxyfluorescein dye (FAM);
RM represents a photoactive reactive moiety; and
$L^1$-$L^3$ represents optional linkers.

5.3.5 Specifically Labeled Proteins

Also, provided herein are proteins, capable of binding a target analyte of interest, that can be specifically labeled in close proximity to the target analyte binding site, and are substantially unlabeled at other positions. The protein can be any protein, or fragment thereof, that is operative in accordance with the various compositions and methods described herein. For example, in some embodiments, the protein can be an antibody capable of binding a target antigen comprising an epitope. In other embodiments, the protein can be an enzyme capable of binding a target substrate. In yet other embodiments, the protein can be a receptor capable of binding a target ligand. In still other embodiments, the protein can be a signal transduction protein capable of binding a target ligand.

The proteins can be specifically labeled with one or more label moiety(ies). Any of the label moieties previously described can be included on the protein. In embodiments employing two or more label moieties, each label moiety can be the same, or some or all of the label moieties can differ.

For example, in some embodiments the protein can comprise a fluorescent moiety. The fluorescent moiety can comprise any entity that provides a fluorescent signal and that can be used in accordance with the methods and principles described herein. In some embodiments, the protein comprises a quenching moiety capable of quenching the fluorescence of a fluorescent moiety.

The exact distance between the label moiety and the target binding site is not critical and can vary over a broad range. The only requirement is that the label moiety be sufficiently distant from the binding site of the target, so as to not substantially block the analyte and surrogate analyte from binding to the binding site on the protein. In some embodiments, the label can be about 3 to 50 Angstroms from the binding site. In some embodiments, the label can be about 5 to 30 Angstroms from the binding site. In some embodiments, the label can be about 5 to 20 Angstroms from the binding site.

Methods for making labeled proteins generally comprise contacting the protein with a labeling molecule comprising a target moiety, a label moiety, a reactive moiety, and a cleavable tether. The target moiety, label moiety, and reactive moiety are connected to one another such that the target moiety can bind the protein, and the reactive moiety can link the label moiety to the protein. Agents capable of activating the reactive moiety are added to form a covalent linkage between the reactive moiety and the protein. The target moiety can be detached from the protein by a) inducing cleavage of the cleavable tether by a suitable agent or condition as described above, and b) providing conditions that effectively remove the target moiety from the vicinity of the protein, such as by dilution, or by the addition of a surrogate analyte or analyte.

FIGS. 1A through 1E illustrate an exemplary embodiment of a method of making a functionally labeled antibody 100 with a labeling molecule 110. FIG. 1A illustrates contacting the antibody 100 with a labeling molecule 110 comprising an antigen moiety AgM, a label moiety LM, a reactive moiety RM, and a cleavable tether CT connected to the antigen moiety AgM. As will be appreciated by a person skilled in the art, the arrangement of various moieties illustrated in label molecule 110 provided in FIGS. 1A through 1E is merely exemplary, and the various moieties can be connected to each other in any way that permits them to perform their respective functions. FIG. 1B illustrates contacting the antibody 100 with a labeling molecule 110. FIG. 1C illustrates activating the reactive moiety *RM so as to form a covalent linkage between the activated reactive moiety *RM and the antibody 100. FIG. 1D illustrates cleaving the cleavable tether *CT. FIG. 1E illustrates the cleavage products following cleavage of the cleavable tether, e.g., the labeled antibody and the antigen moiety AgM.

In some embodiments, the method further comprises isolating the labeled protein from a cleavage product comprising the target moiety. Methods for isolating proteins from cleavage products are known by those skilled in the art.

Typically, proteins suitable for labeling comprise at least one binding domain for a target analyte and a reactive group capable of reacting with the reactive moiety. Non-limiting examples of suitable proteins, label moieties, reactive moieties, and cleavable tethers are described above.

5.3.6 Surrogate Analyte-Labeled Protein Complex

Also provided herein are surrogate analyte-protein complexes useful for, among other things, as reporter systems for analyte detection. The surrogate analyte-protein complex comprises a labeled protein and labeled surrogate analyte. FIG. 2A illustrates an exemplary surrogate analyte-protein complex wherein the surrogate analyte is a surrogate antigen complexed with a labeled protein, i.e., antibody. In FIG. 2A the antibody is labeled with a fluorescent moiety F and the surrogate antigen sA is labeled with a quenching moiety Q. The labeled F antibody and surrogate antigen sA form a surrogate antigen-antibody complex wherein the quenching moiety Q is positioned so that it is able to quench the fluorescence of the fluorescent moiety F on the antibody. The surrogate antigen-antibody complex is capable of producing a detectable increase in fluorescence upon dissociation of the complex caused by the competitive binding of antigen A to the antibody and the displacement of surrogate antigen sA.

The surrogate analyte can be any labeled organic or inorganic molecule capable of competing with the target of interest (i.e. analyte) for binding the labeled protein and capable of comprising a linker that can be optionally attached to a quenching moiety pr a fluorescent moiety. Non-limiting examples of suitable molecules that can comprise the surrogate analyte include antigens, enzyme substrates, proteins, peptides, carbohydrates, polysaccharides, glycoproteins, hormones, receptors, virus, metabolites, transition state analogs, cofactors, inhibitors, drugs, nutrients, electrolytes growth factors and other biomolecules as well as non-biomolecules capable of binding the labeled protein.

In some embodiments the surrogate analyte comprises cAMP.

The surrogate analyte comprises one or more label moiety(ies). Any of the label moieties previously described can be used to label the surrogate analyte. In embodiments employing two or more label moieties, each label moiety can be the same, or some or all of the label moieties can differ.

In some embodiments, the labeled protein comprises a fluorescent moiety and the surrogate analyte comprises a quenching moiety. The fluorescence signal of the fluorescent moiety can be quenched when the surrogate analyte is bound to the labeled protein. The binding of a target analyte to the labeled protein can displace the surrogate analyte and reduce or eliminate the quenching effect, thereby producing a detectable increase in fluorescence.

In some embodiments, the labeled protein comprises a quenching moiety and the surrogate analyte comprises a fluorescent moiety. The fluorescence signal of the fluorescent moiety can quenched when the surrogate analyte is bound to the labeled protein. The binding of a target analyte to the labeled protein can displace the surrogate analyte and reduce or eliminate the quenching effect, thereby producing a detectable increase in fluorescence.

In some embodiments, surrogate analyte-protein complexes are encapsulated in a particle. Encapsulated surrogate analyte-protein complexes can be used for the detection of intracellular analyte molecules, to increase the local concentration of the surrogate-analyte-protein complexes and/or to sequester the surrogate analyte-protein complexes from agents that would otherwise degrade or inactivate the surrogate analyte-protein complexes.

The surrogate analyte-protein complexes can be encapsulated in nanocapsules, liposomes, microparticles, lipid particles, vesicles, and the like. The particles used to encapsulate the surrogate analyte-protein complexes can be permeable, semi-permeable or impermeable. In some embodiments, the surrogate analyte-protein complex can be encapsulated in semi-permeable nanocapsule having a diameter from 10 to 1000 nanometers. In some embodiments, the porosity of the membrane comprising the particle used to encapsulate the surrogate analyte and the labeled protein is selected to retain the surrogate analyte-labeled protein complex, and at the same time, allow passage of the target analyte. Thus, the porosity of the particle membrane is such that it allows passage of elements that are less than or equal to 0.5 nm to 5.0 nm in diameter. In some embodiments, the pore diameter of the particles is less than or equal to 5.0 nm. In some embodiments, the pore diameter of the particles is less than or equal to 2.0 nm. In some embodiments, the pore diameter of the particles is less than or equal to 1.5 nm. In some embodiments, the pore diameter of the particles is less than or equal to 1.0 nm. In some embodiments, the pore diameter of the particles is less than or equal to or equal to 0.5 nm.

In some embodiments, the nanocapsule membrane comprises a cross-linked water soluble vinyl polymer or copolymer. Suitable types of vinyl polymer or copolymer include, but are not limited to, polyvinyl pyrrolidone, polyacrylic acid, polyacrylamide, poly-N,N-dimethylacrylamide, and polyhydroxyethylmethacryate.

The pore diameter of the nanocapsule can be designed to retain the surrogate analyte-protein complex, the labeled protein, and/or the labeled protein-target analyte complex and allow the surrogate analyte or the target analyte to pass through the nanocapsule. For example, in some, embodiments, the nanocapsule is permeable to a target analyte and/or a surrogate analyte and is impermeable to a labeled antibody or fragment thereof. In some embodiments, the nanocapsule is permeable to a target analyte and/or a surrogate analyte and is impermeable to a labeled enzyme or fragment thereof. In some, embodiments, the nanocapsule is permeable to a target analyte and/or a surrogate analyte and is impermeable to a receptor or fragment thereof.

In some embodiments, a targeting moiety can be attached to the nanocapsule and used, for example, to target the nanocapsule to a particular cell or collection of cells. As used herein, "targeting moiety" includes any chemical moiety capable of binding to, or otherwise transporting through, a particular type of membrane and/or organelle in a cell, tissue, or organ. A variety of agents that direct compositions to particular cells are known in the art (see, for example, Cotten et al., Methods Enzym, 217: 618, 1993), and U.S. Pat. Nos; 6,692,911, 6,835,393). Suitable non-limiting examples of targeting moieties include proteins (such as insulin, EGF, or transferrin), lectins, antibodies and fragments, carbohydrates, lipids, oligonucleotides, DNA, RNA, or small molecules and drugs. Additional examples, of useful targeting moieties include, but are in no way limited to, transfection agents such as Pro-Ject (Pierce Biotechnology), viral peptide fragments such as transportans, pore forming toxins such as streptolysin-O, hydrophobic esters, polycations such as polylysine, asiaglycoproteins, and diphtheria toxin.

In some embodiments, the surrogate analyte-protein complexes or the labeled proteins are immobilized on, or attached to, a substrate, such as a solid support or a solid surface. The solid support can be any material known to those of ordinary skill in the art that can be utilized in the assays systems described herein. In general, the support will be amenable to the detection system of choice (e.g. fluorescence when fluors are used as the label.). Suitable solid support include metal surfaces such as gold, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers. In some embodiments, the solid support can allow high throughput screening, such as microtiter plates and beads (sometimes referred to herein as microspheres). The composition of the beads will vary, depending on the use. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used.

Methods for coupling molecules to a solid support are well known in the art and have been widely used in the making of affinity columns, ELISA assay plates, support-bound peptide and drug candidate libraries and polynucleotide arrays. See, for example, Sigel et al., FEBS LETT. 147: 45-48 (1982). Any of the various chemistries and methodologies can be used to immobilize the surrogate analyte or labeled protein. The surrogate analyte or labeled protein can be stably attached to a solid substrate by covalent and/or non-covalent interactions. For instance, the surrogate analyte or labeled protein can be covalently deposited to the surface of a solid support via cross-linking agents, such as glutaraldehyde, borohydride, or other bifunctional agents. The surrogate analyte or labeled protein may also be covalently linked to the substrate via an alkylamino-linker group or a polymer linker. The coupling methods should not substantially affect the binding specificity and/or affinity between the target and the surrogate analyte or labeled protein.

5.3.7 Assays

Also provided herein are assays for detecting the presence or absence of a target analyte in a sample. The sample to be tested can be any suitable sample selected by the user. The sample can be naturally occurring or man-made. For example, the sample can be a blood sample, tissue sample, cell sample, buccal sample, skin sample, urine sample, water sample, or soil sample. The sample can be from a living organism, such as a eukaryote, prokaryote, mammal, human, yeast, or bacterium. The sample can be a cell, tissue, or organ. The sample can be processed prior to contact with a surrogate analyte-protein complex or labeled protein of the present teachings by any method known in the art. For example, the sample can be subjected to a lysing step, precipitation step, column chromatography step, heat step, etc.

The assays comprise contacting a sample with a "reporter system" comprising a surrogate analyte-protein complex or a labeled protein as described herein. In some embodiments, the reporter system can be encapsulated. In other embodiments, the reporter system can be attached to a solid support.

FIG. 3 illustrates an exemplary reporter system comprising one or more surrogate analyte-protein complexes, each comprising a labeled protein ("reporter labeled antibody") and a surrogate analyte ("quencher labeled antigen"), encapsulated in a semipermeable capsule ("hollow shell") to which can be attached targeting moieties ("cell membrane transporting agent"). The targeting moieties can be used to introduce the capsules comprising the reporter system into a cell of interest. As illustrated in FIG. 3, binding of the surrogate analyte to the labeled antibody quenches the signal from the "reporter". The "reporter" depicted in FIG. 3 can comprise any of the label moieties described herein. Passage of one or more target analytes into the capsule can displace one or more surrogate analytes, generating a measurable increase in fluorescence and indicating the presence of the target analyte.

The assays typically comprise contacting a reporter system with a sample comprising one or more target analytes of interest. In embodiments employing two or more target analytes, each labeled protein comprising the reporter system can be the same, or some, or all of the labeled proteins can differ.

The assays taught herein typically comprise the use of a buffer, such as a buffer described in the "Biological Buffers" section of the 2003 Sigma-Aldrich Catalog. Exemplary buffers include sodium phosphate, sodium acetate, PBS, MES, MOPS, HEPES, Tris (Trizma), bicine, TAPS, CAPS, and the like. The buffer is present in an amount sufficient to generate and maintain a desired pH and/or ionic strength. The pH of the binding buffer can be selected according to the pH dependency of the binding activity. For example, the pH can be from 2 to 12, from 4 to 11, or from 6 to 10. The buffer may also contain any necessary cofactors or agents required for binding. The identities and concentration of such cofactors and/or agents will depend upon the particular assay system and will be apparent to those of skill in the art. The concentration of the labeled proteins present in a reporter system may vary substantially. For example, the assay buffer can comprise from about $10^{-10}$ to $10^{-3}$ labeled proteins. In some embodiments, the assay buffer comprises from about 1 pM to 1 µM labeled proteins. If a plurality of different types of labeled proteins are used, each may comprise in the assay buffer in the above concentration ranges.

The assays typically do not require the presence of detergents or other components. In general, it is desirable to avoid high concentrations of components in the reaction mixture that can adversely affect the fluorescence properties of the reaction product, or that can interfere with the detection of target analytes.

The fluorescence signal can be monitored using conventional methods and instruments. For example, the surrogate analyte-protein complexes of the present teachings can be used in a continuous monitoring phase, in real time, to allow the user to rapidly determine whether an analyte is present in the sample, and optionally, the amount or activity of the analyte. In some embodiments, the fluorescence signal can be measured from at least two different time points. In some embodiments, the signal can be monitored continuously or at several selected time points. Alternatively, the fluorescence signal can be measured in an end-point embodiment in which a signal is measured after a certain amount of time, and the signal is compared against a control signal (sample without analyte), threshold signal, or standard curve.

The amount of the fluorescence signal generated is not critical and can vary over a broad range. The only requirement is that the fluorescence be measurable by the detection system being used. In some embodiments, a fluorescence signal that is at least 2-fold greater than the background signal can be generated upon dissociation of the surrogate analyte-protein complex. In some embodiments, a fluorescence signal that is at least 3-fold greater than the background signal can be generated upon dissociation of the surrogate analyte-protein complex. In some embodiments, a fluorescence signal that is at least 4-fold greater than the background signal can be generated upon dissociation of the surrogate analyte-protein complex. In some embodiments, a fluorescence signal that is at least 5-fold greater than the background signal can be generated upon dissociation of the surrogate analyte-protein complex. In some embodiments, a fluorescence signal between 2 to 10-fold greater than the background signal can be generated upon dissociation of the surrogate analyte-protein complex.

5.3.8 Kits

Also provided are kits for performing the methods of the present teachings. In some embodiments, the kits comprise a labeling molecule comprising a target moiety, a label moiety, a reactive moiety, and a cleavable tether. In some embodiments, the kits can contain a buffer for preparing a reaction mixture that facilitates the protein labeling. In some embodiments, the kit can further comprise chemicals for the activation of the reactive moiety and/or cleaving of the cleavable tether. These other components can be provided separately from each other, or mixed together in dry or liquid form.

In some embodiments, the kit comprises surrogate analyte-protein complex useful for detecting the presence or absence of a target analyte. In some embodiments, the kit comprises an encapsulated surrogate analyte-protein complex. In some embodiments, the kit comprises a surrogate analyte-protein complex that is attached to a solid support. In some embodiments, the kit comprises a surrogate analyte that is attached to a solid support. In some embodiments, the kit comprises a labeled protein that is attached to a solid support.

All publications and patent applications mentioned herein are hereby incorporated by reference as if each publication or patent application was specifically and individually indicated to be incorporated by reference. The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those skilled in the art.

What is claimed is:

1. A labeling molecule useful for specifically labeling a protein comprising:
   (a) a target moiety;
   (b) a label moiety;
   (c) a photo-activatable reactive moiety; and
   (d) a cleavable tether linking the target moiety to the label moiety;
   wherein the target moiety, label moiety, and reactive moiety are connected to one another such that the target moiety can bind the protein and the reactive moiety can crosslink the labeling molecule to the protein, and wherein the cleavable tether can be cleaved to allow detachment of the target moiety from the protein thereby resulting in a labeled moiety.

2. The labeling molecule of claim 1 in which the protein is an antibody and the target moiety is an antigen comprising an epitope recognized by said antibody.

3. The labeling molecule of claim 2 which has the structure:

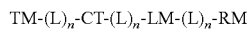

TM-(L)$_n$-CT-(L)$_n$-LM-(L)$_n$-RM wherein:
   TM represents the target moiety;
   CT represents the cleavable tether;
   LM represents the label moiety;
   RM represents the reactive moiety;
   L represents an optional linker moiety; and
   n is an integer from 0 to 5.

4. The labeling molecule of claim 3 in which the label moiety comprises a fluorescent moiety.

5. The labeling molecule of claim 4 in which the fluorescent moiety comprises a xanthene dye.

6. The labeling molecule of claim 5 in which the xanthene dye is selected from a fluorescein dye and a rhodamine dye.

7. The labeling molecule of claim 3 in which the label moiety comprises a quenching moiety.

8. The labeling molecule of claim 7 in which the quenching moiety is capable of quenching the fluorescence of a fluorescent moiety.

9. The labeling molecule of claim 3 in which the reactive moiety is specifically photo-activatable.

10. The labeling molecule of claim 1, wherein the reactive moiety comprises a benzophenone.

11. The labeling molecule of claim 3 in which the reactive moiety is linked to the label moiety via a linker moiety.

12. The labeling molecule of claim 11 in which the linker moiety comprises one or more nitrogen atoms.

13. The labeling molecule of claim 3 in which the cleavable tether comprises a cleavage moiety linked to one or more linker moieties, said cleavage moiety comprising a linkage that can be cleaved by a chemical cleaving agent.

14. The labeling molecule of claim 13 in which the chemical cleaving agent is fluoride.

15. The labeling molecule of claim 13 in which the cleavable tether has the structure:

(TE)$_n$CM(TE)$_n$ wherein:
   CM represents the cleavage moiety;
   TE represents an optional tether element; and
   n is an integer from 0 to 5.

16. The labeling molecule of claim 15 in which tether elements are the same.

17. The labeling molecule of claim 15 in which tether elements are different.

18. The labeling molecule of claim 15 in which the tether elements comprise a substituted or unsubstituted, saturated or unsaturated hydrocarbon, having from 2 to 25 carbon atoms.

19. The labeling molecule of claim 15 in which the tether elements comprise a substituted or unsubstituted, saturated or unsaturated hydrocarbon, having from 2 to 10 carbon atoms.

20. The labeling molecule of claim 18 or 19 in which the tether elements are a linear, branched or cyclic, saturated or unsaturated alkyl.

21. The labeling molecule of claim 20 in which the tether elements is fully saturated n-alkyl.

22. The labeling molecule of claim 18 or 19 further comprising a substituted or unsubstituted heteroatom.

23. The labeling molecule of claim 15 in which the cleavable moiety comprises the structure:

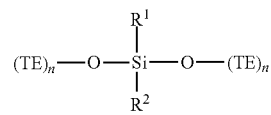

wherein:
   $R^1$ and $R^2$ are hydrocarbons;
   TE represents an optional tether element; and
   n is an integer from 0 to 5.

24. The labeling molecule of claim 1 in which the label moiety, reactive moiety, and target moiety, are linked to one another via a multivalent linker.

25. The labeling molecule of claim 1, wherein the protein to be labeled comprises an enzyme having an active site, wherein said target moiety binds to the enzyme without interfering with the binding of a substrate to the active site of the enzyme.

26. The labeling molecule of claim 1, wherein the protein to be labeled comprises a receptor, wherein said target moiety binds to the receptor without interfering with the binding of a ligand to the receptor.

27. The labeling molecule of claim 1, wherein the protein to be labeled is a signal transduction protein, wherein said target moiety binds to signal transduction protein without interfering with the binding of a ligand to the signal transduction protein.

* * * * *